US011554220B2

(12) United States Patent
Okihara

(10) Patent No.: US 11,554,220 B2
(45) Date of Patent: Jan. 17, 2023

(54) SYRINGE BARREL, METHOD FOR MANUFACTURING SAME, AND PRE-FILLED SYRINGE

(71) Applicant: TERUMO KABUSHIKI KAISHA, Tokyo (JP)

(72) Inventor: Hitoshi Okihara, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 563 days.

(21) Appl. No.: 16/159,079

(22) Filed: Oct. 12, 2018

(65) Prior Publication Data

US 2019/0046736 A1 Feb. 14, 2019

Related U.S. Application Data

(63) Continuation of application No. PCT/JP2017/006946, filed on Feb. 23, 2017.

(30) Foreign Application Priority Data

Apr. 15, 2016 (JP) .............................. JP2016-082159

(51) Int. Cl.
*A61M 5/31* (2006.01)
*A61M 5/28* (2006.01)
(Continued)

(52) U.S. Cl.
CPC ............. *A61M 5/3134* (2013.01); *A61M 5/28* (2013.01); *A61M 5/31* (2013.01); *A61M 5/3202* (2013.01);
(Continued)

(58) Field of Classification Search
CPC .... A61M 2005/3104; A61M 2005/312; A61M 5/3134; A61M 2205/0216; A61M 5/28;
(Continued)

(56) References Cited

U.S. PATENT DOCUMENTS 5,624,402 A 4/1997 Imbert
2012/0109072 A1 5/2012 Tabata et al.
(Continued)

FOREIGN PATENT DOCUMENTS

CN 101879339 A 11/2010
CN 103492002 A 1/2014
(Continued)

OTHER PUBLICATIONS

Office Action dated Apr. 28, 2020 in corresponding Japanese Patent Application No. 2018-511914.
(Continued)

*Primary Examiner* — Shefali D Patel
(74) *Attorney, Agent, or Firm* — Foley & Lardner LLP

(57) ABSTRACT

A syringe barrel includes: a barrel body including a nozzle portion at a distal end thereof; and a cap removably mounted to the nozzle portion and configured to seal a distal end opening of the nozzle portion. The cap includes: an inner cap formed of an elastic material and configured to come in liquid tight contact with the nozzle portion in a mounted state in which the cap is mounted to the nozzle portion, and a cylindrical outer cap formed of a material having a higher hardness than the inner cap and fixed around the inner cap. The inner cap includes: a base portion, and a cylindrical wall extending from the base portion in a proximal direction and surrounding the nozzle portion.

15 Claims, 11 Drawing Sheets

(51) Int. Cl.
 *A61M 5/50* (2006.01)
 *A61M 39/20* (2006.01)
 *A61M 5/32* (2006.01)

(52) U.S. Cl.
 CPC ........... *A61M 5/5086* (2013.01); *A61M 39/20* (2013.01); *A61M 2005/312* (2013.01); *A61M 2005/3104* (2013.01); *A61M 2005/3107* (2013.01); *A61M 2205/3306* (2013.01); *A61M 2207/00* (2013.01)

(58) Field of Classification Search
 CPC .............. A61M 5/3129; A61M 5/3202; A61M 5/5086; A61M 39/20; A61M 2005/3103; A61M 2005/3107; A61M 2005/3109; A61M 2207/00
 See application file for complete search history.

(56) References Cited

U.S. PATENT DOCUMENTS

2013/0237911 A1   9/2013   Von Schuckmann
2014/0358078 A1   12/2014  Fischer et al.
2015/0246185 A1   9/2015   Heinz

FOREIGN PATENT DOCUMENTS

| CN | 104132038 A | 11/2014 |
| CN | 105102046 A | 11/2015 |
| EP | 0 716 860 A | 6/1996 |
| JP | 2736245 B2 | 1/1998 |
| JP | 2005-230458 A | 9/2005 |
| JP | 2006-016053 A | 1/2006 |
| PL | 209749 B | 10/2011 |
| WO | WO-2010/024209 A1 | 3/2010 |
| WO | WO-2011/008190 A1 | 1/2011 |
| WO | WO-2011/108574 A1 | 9/2011 |
| WO | WO-2014/190225 A | 11/2014 |

OTHER PUBLICATIONS

Extended European Search Report dated Sep. 25, 2019 for corresponding Application No. 17782131.1.
Chinese Office Action dated May 6, 2021 in Chinese Patent Application No. 201780022160.8 (7 pages).

SYRINGE BARREL, METHOD FOR MANUFACTURING SAME, AND PRE-FILLED SYRINGE

CROSS-REFERENCE TO RELATED APPLICATIONS

The present application is a bypass continuation of PCT Application No. PCT/JP2017/006946, filed on Feb. 23, 2017, which claims priority to Japanese Application No. 2016-082159, filed on Apr. 15, 2016. The contents of these applications are hereby incorporated by reference in their entireties.

BACKGROUND

The present disclosure relates to a syringe barrel, a syringe barrel manufacturing method, and a pre-filled syringe.

In a conventional pre-filled syringe that is pre-filled with a liquid, a cap to close a nozzle portion in a liquid tight manner is mounted to a distal end of a barrel in order to inhibit leakage of a liquid inside the syringe from a syringe distal end opening prior to use of the syringe, particularly during transportation (refer to, for example, JP 2736245 B2).

The cap disclosed in JP 2736245 B2 includes an inner cap formed of an elastic material and a hard outer cap fixed around the inner cap, with an outer screw provided on the outer cap being configured to be engaged with an inner screw provided at a Luer collar fixed at a distal end portion of a syringe barrel, so as to cause the inner cap to seal the distal end portion of the syringe barrel in a liquid tight manner.

SUMMARY

In the case of the cap disclosed in JP 2736245 B2, even slight movement of the cap in a distal direction with respect to the syringe barrel would disable the sealing function of the cap, leading to leakage of the liquid to the outside of the cap.

Certain embodiments described in the present disclosure have been developed in consideration of such problems, and aim to provide a syringe barrel, a syringe barrel manufacturing method, and a pre-filled syringe capable of inhibiting leakage of a liquid to the outside of a cap even in a case in which the cap slightly moves in the distal direction with respect to a barrel body.

According to one embodiment, a syringe barrel includes: a barrel body including a nozzle portion at a distal end thereof, a cap removably mounted to the nozzle portion for sealing a distal end opening of the nozzle portion, in which the cap comprising: an inner cap formed of an elastic material and configured to be in liquid tight contact with the nozzle portion in a mounted state in which the cap is mounted to the nozzle portion; and a cylindrical outer cap formed of a material having higher hardness than the inner cap and fixed around the inner cap, the inner cap comprises: a base portion; and a cylindrical wall extending from the base portion in a proximal direction and surrounding the nozzle portion, the cylindrical wall is configured to be sandwiched in a compressed state between an outer peripheral surface of the nozzle portion and an inner peripheral surface of the outer cap in a state in which the base portion is in contact with a distal end surface of the nozzle portion and in a state in which the base portion is apart from the distal end surface of the nozzle portion by a predetermined distance, such that the cylindrical wall is in liquid tight contact over a full circumference with the outer peripheral surface of the nozzle portion.

According to the syringe barrel having the above configuration, the cylindrical wall of the inner cap formed of an elastic material is compressed between the outer peripheral surface of the nozzle portion and the inner peripheral surface of the outer cap even in a case in which the cap slightly moves in the distal direction from the state of contact with the distal end surface of the nozzle portion. This configuration allows contact between the outer peripheral surface of the nozzle portion and the inner peripheral surface of the cylindrical wall, forming a liquid tight seal at a contact portion. Accordingly, it is possible to effectively inhibit leakage of the liquid in the barrel body to the outside of the cap.

In one aspect of the syringe barrel described above, an axial length of a compressed portion, which is a portion of the cylindrical wall compressed between the nozzle portion and the outer cap in a state in which the base portion is in contact with the distal end surface of the nozzle portion, may be 0.5 mm or more.

This configuration appropriately increases a length of a liquid tight seal due to the contact between the cylindrical wall and the nozzle portion, making it possible to suitably inhibit leakage of a drug solution to the outside of the cap. Furthermore, for example, it is possible to reliably inhibit liquid leakage in a pre-filled syringe determined to be a non-defective product in a case in which a loosening length threshold for determining acceptance in the cap mounting inspection is 0.5 mm.

In one aspect of the syringe barrel described above, the compressed portion may include an enlarged diameter portion protruding outward in a radial direction more than the other portion of the cylindrical wall.

This configuration can easily increase a contact area (liquid tight seal area) between the cylindrical wall and the nozzle portion.

In one aspect of the syringe barrel described above, the inner peripheral surface of the cylindrical wall may have a shape substantially corresponding to the outer peripheral surface of the nozzle portion.

With this configuration, the axial length of the contact portion between the cylindrical wall and the nozzle portion is longer than the axial length of the enlarged diameter portion, making it easier to increase the contact area between the cylindrical wall and the nozzle portion (liquid tight seal area).

In one aspect of the syringe barrel described above, the axial length of the compressed portion may be shorter than the axial length of the cylindrical wall.

With this configuration, it is possible to effectively deter an increase in a cap opening torque (torque needed to turn the cap for opening the cap) due to the presence of the compressed portion.

In one aspect of the syringe barrel described above, the compressed portion may be disposed at a distal end portion of the cylindrical wall.

This configuration forms a liquid tight seal at the distal end portion of the outer peripheral surface of the nozzle portion, making it possible to further effectively inhibit liquid leakage to the outside of the cap.

In one aspect of the syringe barrel described above, a compressibility of the compressed portion, which a portion of the cylindrical wall compressed between the nozzle portion and the outer cap in the mounted state, may be 5% to 50%.

With this configuration, it is possible to effectively inhibit an excessive increase in the opening torque of the cap while holding satisfactory pressure resistance.

In one aspect of the syringe barrel described above, a diameter of the distal end opening of the nozzle portion may be 1.5 mm or more.

With a relatively large diameter of the distal end opening of the nozzle portion, a large pressure would be applied to the inner cap even in a state in which the cap is tightly closed (state in which the inner cap and the distal end surface of the nozzle portion are in contact with each other), leading to a high probability of liquid leakage in the absence of the compressed portion. This aspect is particularly useful in that liquid leakage can be effectively inhibited by the presence of the compressed portion even in a case in which the diameter of the distal end opening of the nozzle portion is as relatively large as 1.5 mm or more.

In one aspect, the barrel body includes: a lock adapter disposed on an outer side of the nozzle portion; and an annular recess disposed between the nozzle portion and the lock adapter and recessed in a proximal direction, the outer cap includes a proximal end cylindrical portion covering the cylindrical wall, the proximal end cylindrical portion of the outer cap includes an engaging portion on an inner peripheral surface of the proximal end cylindrical portion, the engaging portion being configured to engage with the cylindrical wall, wherein, in the mounted state, the cylindrical wall of the inner cap and the proximal end cylindrical portion of the outer cap are configured to be inserted into the annular recess, and the inner peripheral surface of the cylindrical wall is configured to be in contact with the outer peripheral surface of the nozzle portion, and when the cap in the mounted state is removed from the barrel body, engagement between the engaging portion and the cylindrical wall allows a moving force of the outer cap to move with respect to the lock adapter to be transmitted directly to the cylindrical wall.

According to this configuration, it is possible to move the inner cap together with the movement of the outer cap at removal of the cap from the barrel body even in a case in which the inner peripheral surface of the cylindrical wall of the inner cap is pseudo fixed (adhered) to the outer peripheral surface of the nozzle portion, making it possible to deter expansion of the cylindrical wall. This makes is possible to inhibit the drug solution from spouting out at the time of opening the cap.

In one aspect, the engaging portion is an engaging protrusion that protrudes inward in a radial direction from the inner peripheral surface of the proximal end cylindrical portion of the outer cap, and the cylindrical wall includes an engaged portion that is configured to be engaged with the engaging protrusion, and when the cap in the mounted state is removed from the barrel body, engagement of the engaging protrusion with the engaged portion from the proximally allows the moving force to be transmitted directly to the cylindrical wall.

This configuration enables acquisition of a further satisfactory engaging force, making it possible to further reliably move the inner cap together with the movement of the outer cap when the cap is removed from the barrel body.

In one aspect, the engaged portion may be a proximal end surface of the cylindrical wall.

With this configuration, the proximal end surface of the cylindrical wall is pressed in the distal direction by the engaging portion when the cap is removed from the barrel body, making it possible to move the entire cylindrical wall integrally with the outer cap. In addition, the proximal end surface of the cylindrical wall can be utilized as it is as the engaged portion, making it possible to avoid structural complication of the cylindrical wall due to the presence of the engaged portion.

In one aspect, the engaged portion may be an engaged protrusion that protrudes outward in the radial direction from the outer peripheral surface of the cylindrical wall.

This configuration enables acquisition of a further satisfactory engaging force, making it possible to further reliably move the inner cap together with the movement of the outer cap when the cap is removed from the barrel body.

In one aspect, the lock adapter includes a female screw portion on an inner peripheral surface of the lock adapter, the outer cap includes a male screw portion that is disposed on the outer peripheral surface of the proximal end cylindrical portion, the male screw portion being configured to screw with the female screw portion, the female screw portion and the male screw portion are configured to be screwed with each other in the mounted state, the engaging portion is a plurality of engaging ribs extending along an axis of the proximal end cylindrical portion, the cylindrical wall includes an engaged portion that is disposed on the outer peripheral surface of the cylindrical wall, the engaged portion being configured to be engaged with the plurality of engaging ribs, and when the outer cap is rotated with respect to the lock adapter to remove the cap in the mounted state from the barrel body, engagement of the plurality of engaging ribs with the engaged portion allows the moving force of the outer cap to rotationally move with respect to the lock adapter to be transmitted directly to the cylindrical wall.

This configuration causes the cylindrical wall of the inner cap to rotate simultaneously with the outer cap when the cap is removed from the barrel body, making it possible to further reliably move the inner cap together with the movement of the outer cap.

In one aspect, the barrel body may be formed of a cyclic olefin polymer or a cyclic olefin copolymer.

With the barrel body formed of a cyclic olefin polymer or a cyclic olefin copolymer, the inner cap is likely to be pseudo fixed to the nozzle portion. Accordingly, according to this aspect, it is possible to inhibit expansion of the cylindrical wall at the time of opening the cap is particularly useful.

In one aspect, the inner cap may be formed from butyl rubber.

With the barrel body formed from butyl rubber, the inner cap is further likely to be pseudo fixed to the nozzle portion. Accordingly, in this aspect, it is possible to inhibit expansion of the cylindrical wall at the time of opening the cap is particularly useful.

In one aspect, sterilization treatment, in which the syringe barrel is heater, may be applied on the syringe barrel in the mounted state.

With application of sterilization treatment involving heating, the inner cap is further likely to be pseudo fixed to the nozzle portion. Accordingly, in this aspect, it is possible to inhibit expansion of the cylindrical wall at the time of opening the cap is particularly useful.

According to another embodiment, a pre-filled syringe includes: any one of the syringe barrels described above; a gasket slidably inserted in the barrel body; a plunger that is coupled or couplable to the gasket, and a drug solution filled in a liquid chamber formed by the barrel body and the gasket.

According to another embodiment, a syringe barrel manufacturing method accoincudes: an assembling step of mounting the cap to the barrel body to assemble a barrel assembly; a photographing step of photographing a reference portion of the barrel body and a reference portion of the cap as one image using a camera; and a determination step of determining that the barrel assembly is a non-defective product if a distance between the reference portion of the barrel body and the reference portion of the cap is a predetermined value or less in the image photographed by the camera, in which an axial length of a compressed portion, which is a portion of the cylindrical wall compressed between the nozzle portion and the outer cap in a state in which the base portion is in contact with the distal end surface of the nozzle portion, is the predetermined value or more.

With the syringe barrel, the syringe barrel manufacturing method, and the pre-filled syringe according to certain embodiments of the present disclosure, it is possible to inhibit the leakage of a liquid to the outside of the cap even in a case in which the cap slightly moves in the distal direction with respect to the barrel body.

DETAILED DESCRIPTION

Embodiments of a syringe barrel, a syringe barrel manufacturing method, and a pre-filled syringe will be described below with reference to the accompanying drawings.

First Embodiment

Figure 1:
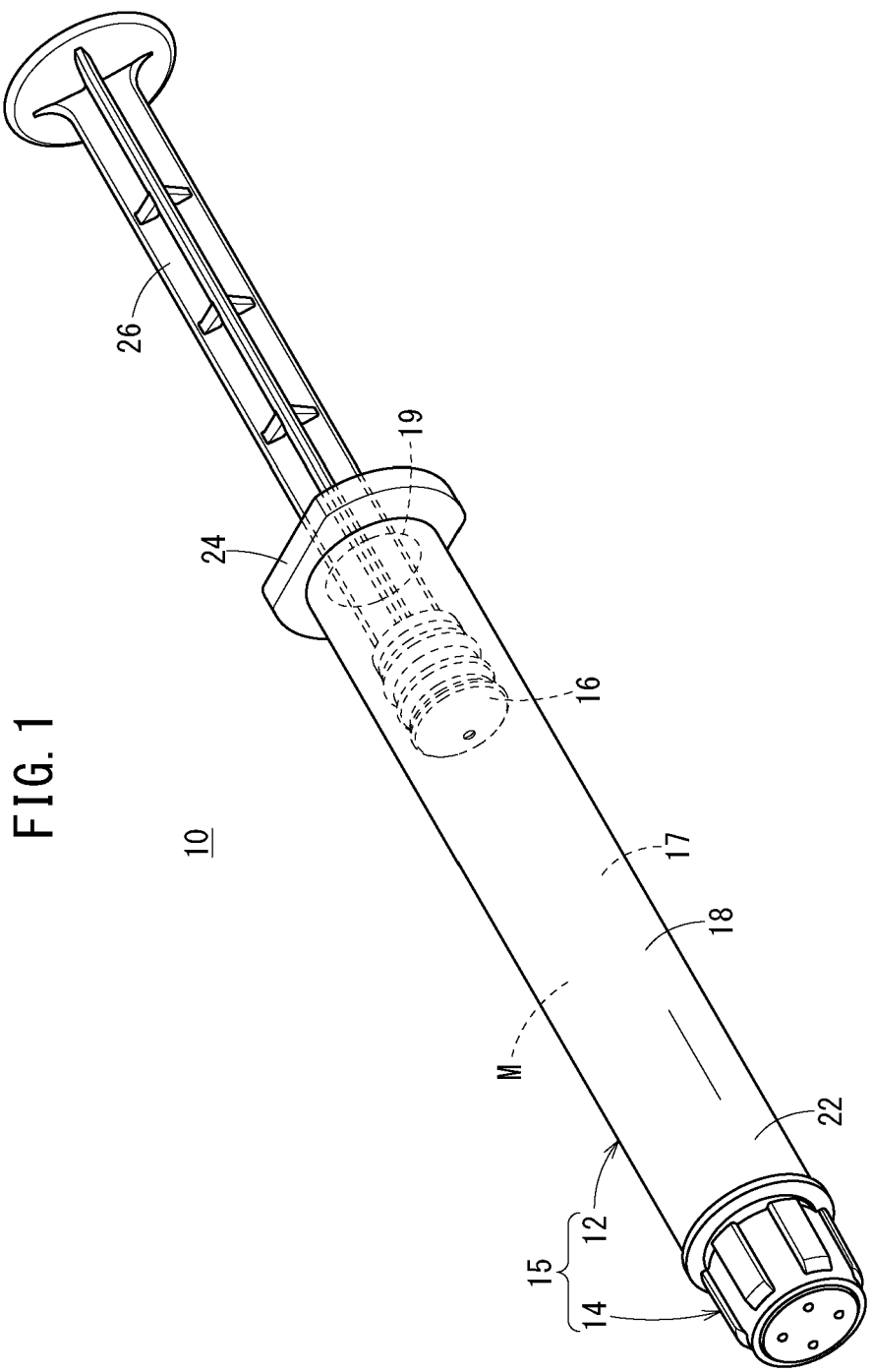
FIG. 1 is a perspective view of a pre-filled syringe according to a first embodiment.

A pre-filled syringe 10 according to a first embodiment illustrated in FIG. 1 includes, as main components: a barrel body 12 formed of a hollow body provided with a nozzle portion 20; a cap 14 for sealing the nozzle portion 20 of the barrel body 12; a gasket 16 slidably inserted in the barrel body 12; and a drug solution M filled in a liquid chamber 17 formed by the barrel body 12 and the gasket 16. The barrel body 12 and the cap 14 constitute a syringe barrel 15.

The barrel body 12 includes: a body portion 18 having a substantially cylindrical shape and including a proximal end opening 19 formed at a proximal end; a nozzle portion 20 (refer to FIG. 2) provided at a distal end of the barrel portion 18; a lock adapter 22 provided on an outer side of the nozzle portion 20; and a flange 24 protruding outward in a radial direction from the distal end of the body portion 18. In the barrel body 12 in the illustrated example, the body portion 18, the nozzle portion 20, the lock adapter 22, and the flange 24 are integrally formed.

The gasket 16 is inserted through the barrel body 12 via the proximal end opening 19. The proximal side of the barrel body 12 is sealed in a liquid tight manner with the gasket 16, and the drug solution M is sealed within the barrel body 12.

The gasket 16 is formed of an elastic material such as a rubber material. The gasket 16 allows its outer peripheral portion to be in liquid tight contact with the inner peripheral surface of the barrel body 12, and is slidably disposed in the barrel body 12. The gasket 16 is coupled with a distal end portion of the plunger 26. Operation of pressing the plunger 26 in the distal direction performed by the user causes the gasket 16 to slide in the distal direction inside the barrel body 12. Note that the plunger 26 may be coupled to the gasket 16 at the time of administration of the drug solution M to a patient.

Figure 2:
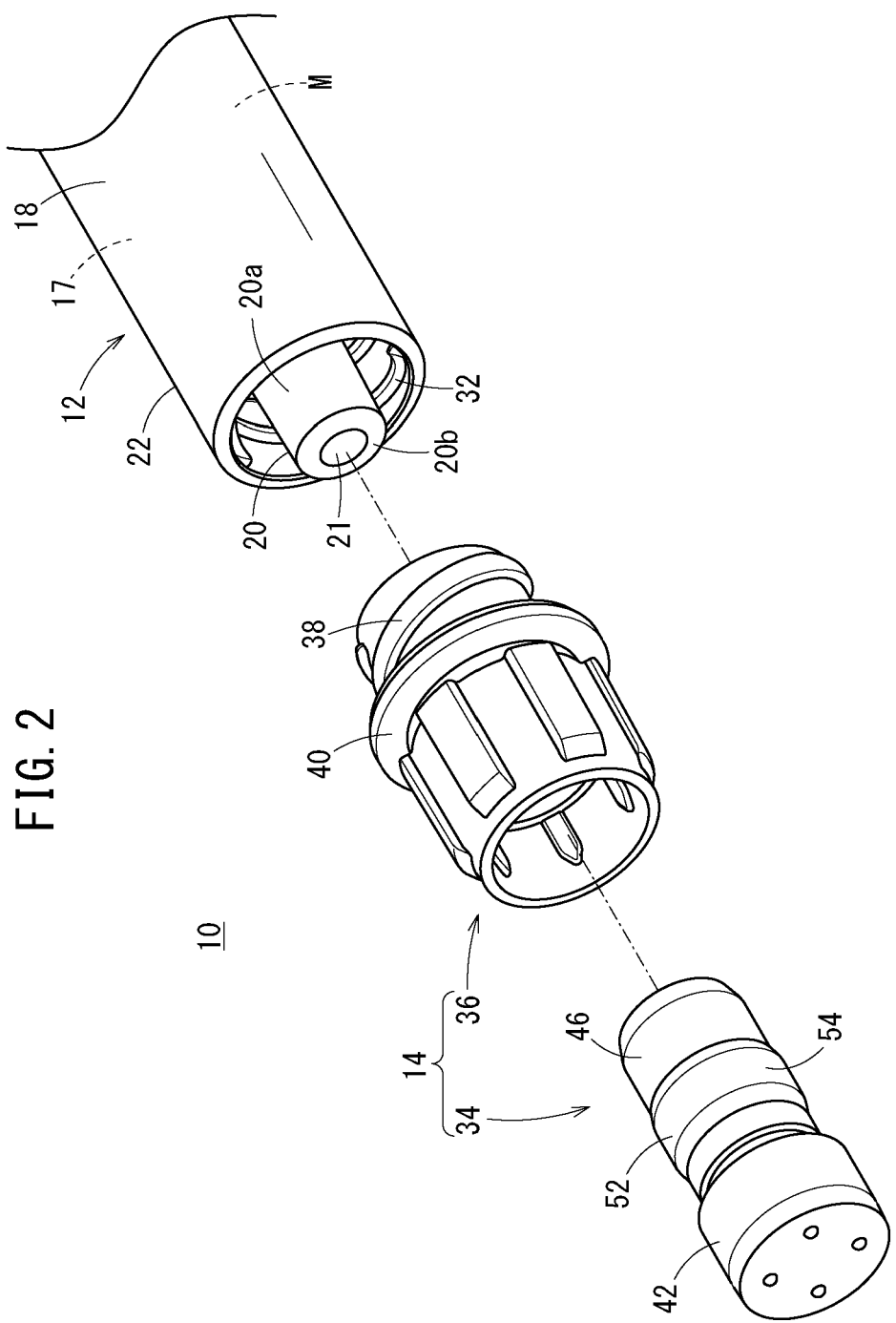
FIG. 2 is an exploded perspective view of a distal end portion of the pre-filled syringe illustrated in FIG. 1.
Figure 3:
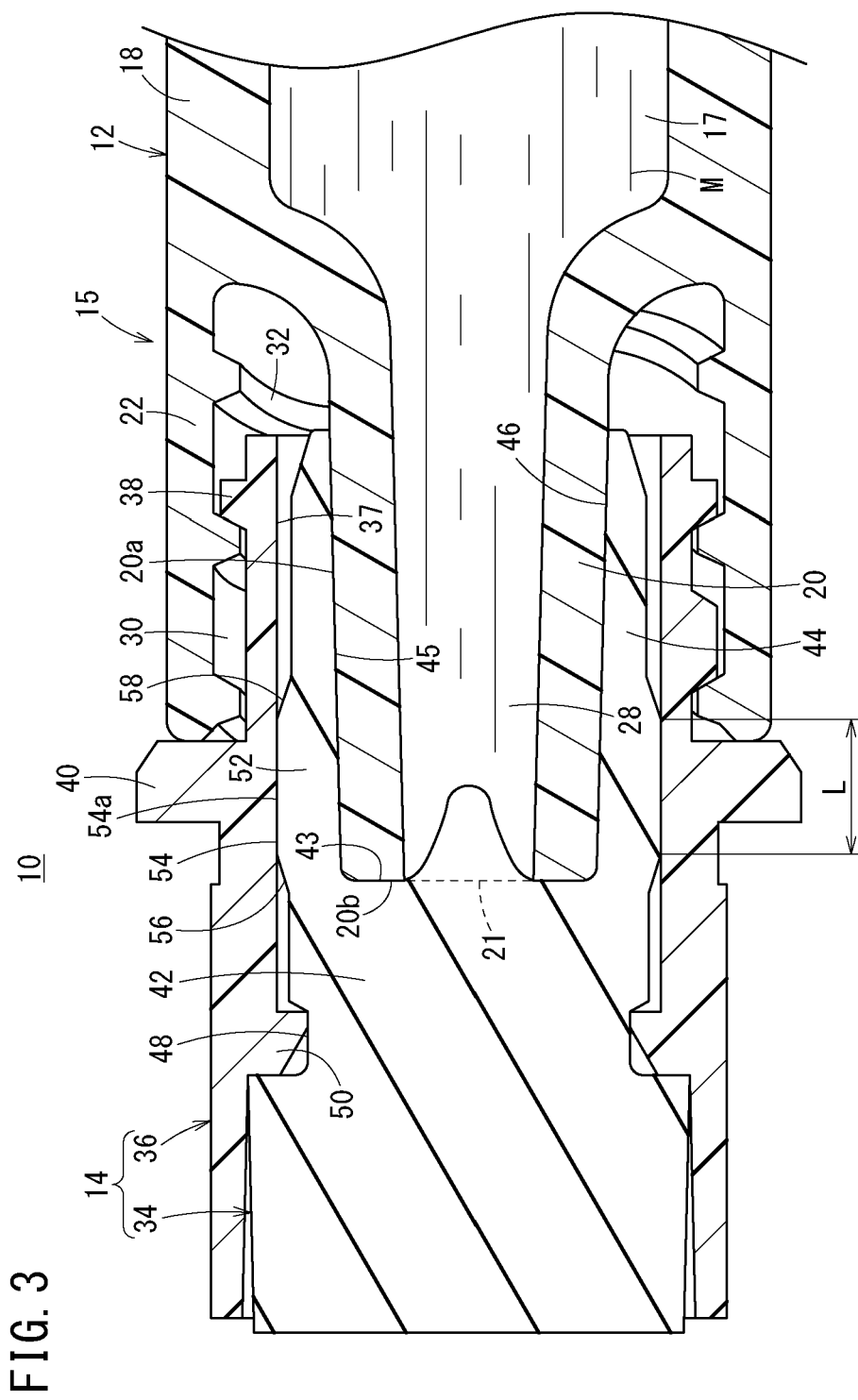
FIG. 3 is a cross sectional view of a distal end portion of the pre-filled syringe illustrated in FIG. 1.

As illustrated in FIG. 2, the nozzle portion 20 is diametrically reduced from the center on the distal end of the barrel body 12 with respect to the barrel body 12 and extends in the distal direction. The nozzle portion 20 includes a tapered outer peripheral surface 20a having outer diameter reducing toward the distal direction. That is, the outer peripheral surface 20a of the nozzle portion 20 constitutes a Luer taper. As illustrated in FIG. 3, the nozzle portion 20 includes a liquid path 28 communicating with the liquid chamber 17 in the barrel body 12 and penetrating in the axial direction. The distal end of the liquid path 28 forms a distal end opening 21 of the nozzle portion 20.

In a state in which the cap 14 is removed from the nozzle portion 20, a needle unit (not illustrated) is detachably located on the nozzle portion 20. The needle unit includes: a needle body having a needle point; and a needle hub having a protrusion fixed to the proximal end portion of the needle body and protruding outward. The nozzle portion 20 can be taper-fitted to an inner peripheral portion of the needle hub. In use of the pre-filled syringe 10, the cap 14 is unplugged (removed from the barrel 20 and the lock adapter 22), and instead the needle hub of the needle unit is connected to the nozzle portion 20 and the lock adapter 22.

The lock adapter 22 in the illustrated example is formed in a substantially hollow cylindrical shape extending in the distal direction from the distal end of the body portion 18 and surrounding the nozzle portion 20. The above-described nozzle portion 20 protrudes distally beyond the lock adapter 22, and forms an annular recess 30 recessed in the proximal direction between the lock adapter 22 and the nozzle portion 20. The inner peripheral surface of the lock adapter 22 includes a female screw portion 32. The female screw portion 32 is removably engaged with a male screw portion 38 (described below) of the cap 14. In a state in which the cap 14 is removed from the barrel body 12, the female screw portion 32 is engageable with a protrusion provided on the needle hub of the above-described needle unit.

While the lock adapter 22 of the illustrated example is integrally formed at the distal end portion of the body portion 18 as a portion of the barrel body 12, the lock adapter 22 may be integrally formed at the proximal end portion of the nozzle portion 20. Alternatively, the lock adapter 22 may be configured as a separate component from the body portion 18 and the nozzle portion 20, and may be a member fixed to the barrel body 12 or the nozzle portion 20.

Examples of the constituent material of the barrel body 12 include various resins such as polypropylene, polyethylene, polystyrene, polyamide, polycarbonate, polyvinyl chloride, poly-(4-methylpentene-1), acrylic resin, acrylonitrile-butadiene-styrene copolymer, polyester such as polyethylene terephthalate, and cyclic polyolefins.

Figure 4:
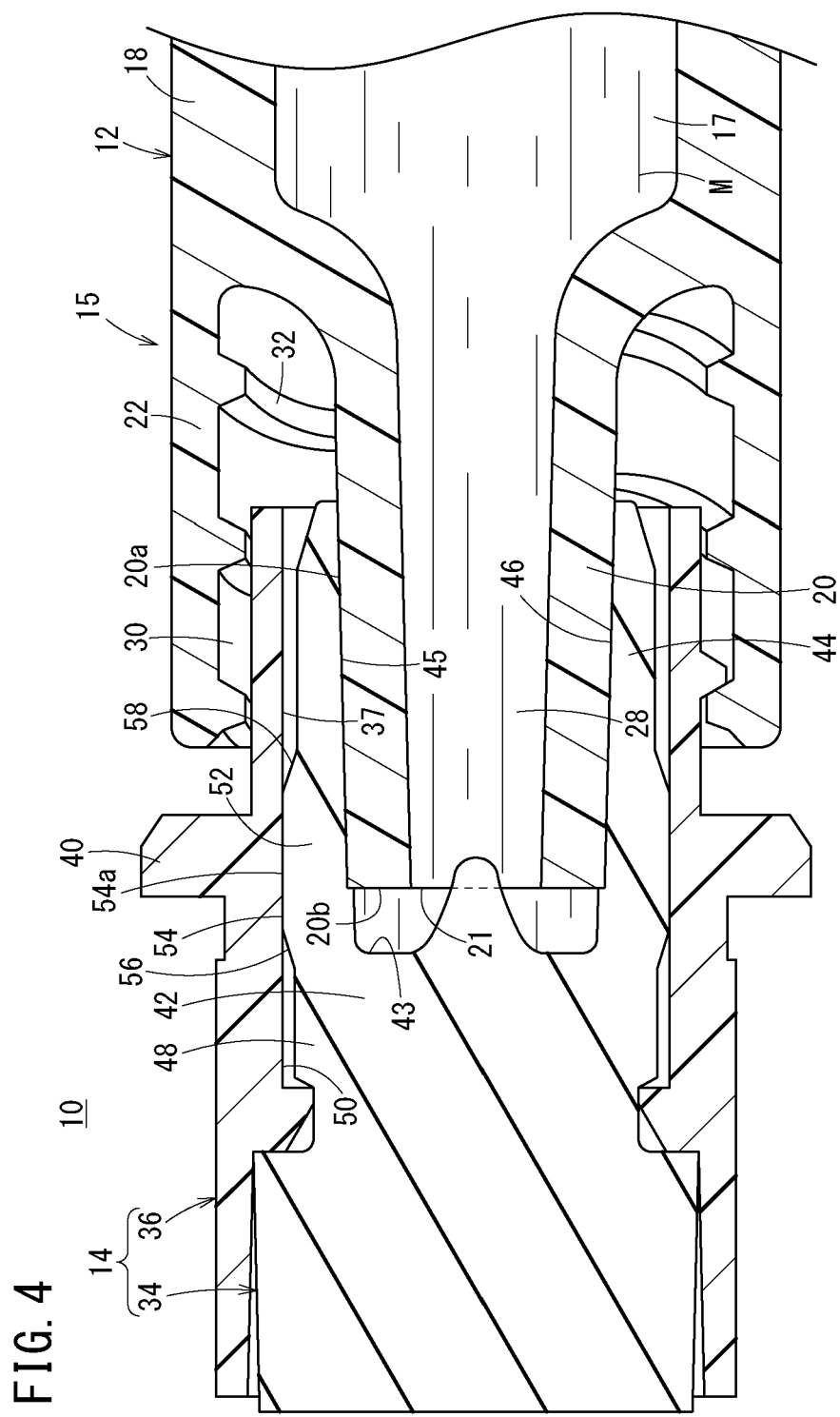
FIG. 4 is a cross sectional view illustrating a state in which a cap has slightly moved in a distal direction from the state of FIG. 3 with respect to a nozzle portion.

The cap 14 is removably mounted to the nozzle portion 20, and seals the distal end opening 21 of the nozzle portion 20. The illustrated cap 14 is detachably provided on the nozzle portion 20. As illustrated in FIGS. 2 to 4, the cap 14 includes: an inner cap 34 for sealing the distal end opening 21; and a hollow cylindrical outer cap 36 for supporting the inner cap 34.

The inner cap 34 is formed of an elastic material. In a state before use (hereinafter also referred to as "mounted state") where the cap 14 is mounted to the nozzle portion 20, the inner cap 34 is in liquid tight contact with the nozzle portion 20 so as to inhibit leakage of the drug solution M to the outside of the cap 14. In FIG. 3, the inner cap 34 is in contact over a full circumference with each of the outer peripheral surface 20a and the distal end surface 20b of the nozzle portion 20.

Examples of the elastic material of the inner cap 34 include various rubber materials such as natural rubber, butyl rubber, isoprene rubber, butadiene rubber, styrene-butadiene rubber, and silicone rubber, or various types of thermoplastic elastomer such as polyurethane type, polyester type, polyamide type, olefin type, and styrene type, or a mixture thereof.

As illustrated in FIGS. 3 and 4, the outer cap 36 is fixed to the outer periphery of the inner cap 34. The male screw portion 38 to be releasably screwed to the female screw portion 32 of the lock adapter 22 is formed on the proximal end outer peripheral portion of the outer cap 36. On a distal side of the male screw portion 38 on the outer peripheral portion of the outer cap 36, there is provided a stopper 40 protruding outward in the radial direction.

In a state in which the cap 14 is firmly (completely) mounted to the nozzle portion 20 and the lock adapter 22, the outer cap 36 is screwed to the lock adapter 22 up to a position where the proximal end surface of the stopper 40 and the distal end surface of the lock adapter 22 are in contact with each other. Accordingly, in the process of assembling the syringe barrel 15, checking the presence or absence and the size of a gap between the stopper 40 and the lock adapter 22 leads to checking whether the cap 14 is satisfactorily mounted to the barrel body 12. While the stopper 40 in the illustrated example is formed in an annular shape over a full circumference in the circumferential direction of the outer cap 36, it is also possible to provide a plurality of the stoppers 40 at intervals in the circumferential direction.

Next, a configuration of the inner cap 34 will be described in more detail. The inner cap 34 includes a base portion 42 located on a distal side of the nozzle portion 20 in the mounted state; and a cylindrical wall 44 extending from the base portion 42 in the proximal direction. The base portion 42 and the cylindrical wall 44 forms a recess 46 recessed in the distal direction. The base portion 42 constitutes a distal side portion of the inner cap 34.

The outer peripheral portion of the base portion 42 includes an annular groove 48 recessed inward in the radial direction, and an annular protrusion 50 provided on the inner peripheral portion of the outer cap 36 is engaged with the annular groove 48. This configuration inhibits a relative movement in the axial direction between the inner cap 34 and the outer cap 36. In FIG. 3, the proximal end surface 43 (the bottom portion of the recess 46) of the base portion 42 is brought into contact over a full circumference with the distal end surface 20b of the nozzle portion 20 and slightly squeezed in the distal direction by the distal end surface 20b.

The cylindrical wall 44 is formed in a hollow cylindrical shape. In the mounted state of the cap 14, the cylindrical wall 44 surrounds the nozzle portion 20. Moreover, the cylindrical wall 44 is sandwiched in a compressed state between the outer peripheral surface 20a of the nozzle portion 20 and the inner peripheral surface 37 of the outer cap 36 in a state in which the base portion 42 is in contact with the distal end surface 20b of the nozzle portion 20 (FIG. 3) and in a state in which the base portion 42 is apart from the distal end surface 20b of the nozzle portion 20 by a predetermined distance (FIG. 4).

This brings the inner peripheral surface 45 of the cylindrical wall 44 into contact over a full circumference with the outer peripheral surface 20a of the nozzle portion 20, so as to form a liquid tight seal at this contact portion in the state illustrated in FIGS. 3 and 4. This inhibits leakage of the drug solution M to the outside of the cap 14 even in a case in which the cap 14 slightly moves in the distal direction from the state of FIG. 3 and where the proximal end surface 43 of the base portion 42 is apart from the distal end surface 20b of the nozzle portion 20 as illustrated in FIG. 4.

Specifically, the cylindrical wall 44 includes a compressed portion 52 compressed in the radial direction (wall thickness direction of the cylindrical wall 44) between the outer peripheral surface 20a of the nozzle portion 20 and the inner peripheral surface 37 of the outer cap 36. Accordingly, the inner peripheral surface of the compressed portion 52 and the outer peripheral surface 20a of the nozzle portion 20 are in contact over a full circumference with each other. In the present embodiment, the compressed portion 52 includes an enlarged diameter portion 54 (refer to also FIG. 2) protruding outward in the radial direction rather than the other portion of the cylindrical wall 44, and is sandwiched between the nozzle portion 20 and the inner peripheral surface 37 of the outer cap 36, so as to form a high-intensity contact portion a having higher degree of contact than other portions.

An outer peripheral surface 54a of the enlarged diameter portion 54 has a constant outer diameter along the axial direction and is in contact with the inner peripheral surface of the outer cap 36 over the entire axial length. The outer peripheral portion of the cylindrical wall 44 includes: a distal side tapered portion 56 continuing to the distal end of the enlarged diameter portion 54 and decreasing an outer diameter toward the distal direction; and a proximal side tapered portion 58 continuing to the proximal end of the enlarged diameter portion 54 and decreasing an outer diameter in the proximal direction. Note that the compressed portion 52 is only required to be sandwiched between the nozzle portion 20 and the inner peripheral surface 37 of the outer cap 36 so as to be able to form a high-intensity contact portion having a higher degree of contact than other portions. Therefore, the compressed portion 52 may include, instead of the enlarged diameter portion 54, a reduced diameter portion protruding inward in a radial direction more than the other portions of the cylindrical wall 44 and provided on the inner peripheral portion of the cylindrical wall 44.

An axial length L (length from the distal end to the proximal end of the outer peripheral surface 54a in contact with the inner peripheral surface 37 of the outer cap 36) of the compressed portion 52 (enlarged diameter portion 54 or the reduced diameter portion) is 0.5 mm or more, for example, and preferably 1.0 mm or more. With the axial length L of the compressed portion 52 set within the above range, it is possible to appropriately increase the length of the liquid tight seal (contact region between the compressed portion 52 and the outer peripheral surface 20a), making it possible to suitably inhibit leakage of the drug solution M to the outside of the cap 14. In the present embodiment, the axial length L is 0.5 mm or more.

In an assembling step of the syringe barrel 15, a cap mounting inspection may be performed to determine whether the cap 14 is satisfactorily mounted to the barrel body 12. In this inspection, a state in which the cap 14 is firmly mounted (FIG. 3) is defined as a reference. A non-defective product is determined in a case in which the cap 14 is loose at a predetermined length (for example, 0.5 mm) or less in the distal direction with respect to the reference. A defective product is determined in a case in which the cap is loose beyond the predetermined length. With the axial length L of the compressed portion 52 set to be longer than the loosening length determined to be non-conforming, it is possible to reliably inhibit liquid leakage in the pre-filled syringe 10 using the syringe barrel 15 determined to be conforming.

Specifically, the manufacturing method of the syringe barrel 15 including such a cap mounting inspection includes an assembling step, a photographing step, and a determination step as follows.

In the assembling step, the cap 14 is mounted to the barrel body 12 to assemble the barrel assembly (syringe barrel 15).

Figure 5:
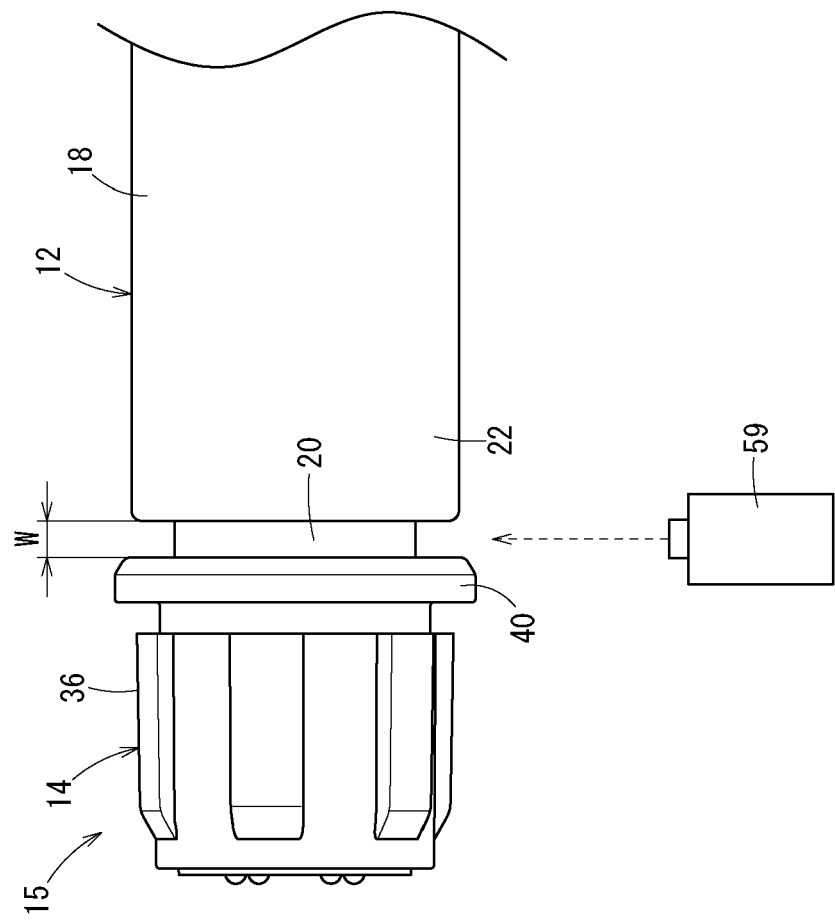
FIG. 5 is a diagram illustrating a photographing step in a syringe barrel manufacturing method.

After completion of the assembling step, the photographing step is next performed. In the photographing step, a reference portion of the barrel body 12 and a reference portion of the cap 14 are photographed by a camera 59 as one image (still image) as illustrated in FIG. 5. In FIG. 5, the reference portion of the barrel body 12 is the distal end of the lock adapter 22, while the reference portion of the cap 14 is the proximal end of the stopper 40 of the outer cap 36. A portion other than the distal end of the lock adapter 22 in the barrel body 12 may be set as a reference portion and a portion other than the proximal end of the stopper 40 in the outer cap 36 may be set as the reference portion.

After completion of the photographing step, a determination step is performed. The determination step determines the barrel assembly as a non-defective product in a case in which a distance W between the reference portion of the barrel body 12 and the reference portion of the cap 14 is a predetermined value or less (for example, 0.5 mm or less) in the image photographed by the camera 59. This determination is automatically made by a determination apparatus (computer) having an image processing function. The determination apparatus specifies the reference portion of the barrel body 12 and the reference portion of the cap 14 from the obtained image, for example using pattern matching, for example, and measures the distance between the reference portions. Then, the determination apparatus determines whether the barrel assembly is conforming or non-conforming on the basis of the obtained distance. The axial length L (refer to FIG. 3) of the compressed portion 52 described above is the predetermined value or more.

In the present embodiment, the axial length L of the compressed portion 52 is shorter than the axial length of the cylindrical wall 44. This makes it possible to deter difficulty in opening the cap 14 due to an increase in opening torque of the cap 14 (torque required for turning the cap 14 to open). From such a viewpoint, the axial length L of the compressed portion 52 is set to, for example, 5 mm or less, preferably 3 mm or less, and more preferably 2 mm or less. The axial length L of the compressed portion 52 may be the same as the axial length of the cylindrical wall 44 unless emphasis is placed on the opening torque of the cap 14.

Furthermore, in the present embodiment, the compressed portion 52 is provided at the distal end portion of the cylindrical wall 44. This configuration forms a liquid tight seal at the distal end portion of the outer peripheral surface 20a of the nozzle portion 20, making it possible to further effectively inhibit leakage of the drug solution M to the outside of the cap 14. The compressed portion 52 may be provided in the proximal side region of the cylindrical wall 44.

In the mounted state of the cap 14, the compressibility of the compressed portion 52 is, for example, 5% to 50%, preferably 10% to 20%. Here, the compressibility of the compressed portion 52 represents a ratio of the amount of strain to the thickness of the compressed portion 52 in the natural state (state in which the compressed portion 52 is not sandwiched between the nozzle portion 20 and the outer cap 36). When the amount of strain is δ, the thickness of the compressed portion 52 in the natural state is T0, and the thickness of the compressed portion 52 in the compressed state is T1, δ=T0−T1 holds.

With the compressibility of less than 5%, the degree of contact between the cylindrical wall 44 and the nozzle portion 20 might become weak, leading to a failure in obtaining desired pressure resistance performance. On the other hand, the compressibility exceeding 50% might excessively increase the opening torque of the cap 14, making it difficult to open the cap 14. By setting of the compressibility 5% to 50%, it is possible to effectively deter the cap opening torque of the cap 14 from becoming excessively large while maintaining satisfactory pressure resistance performance.

As described above, according to the syringe barrel 15 (pre-filled syringe 10), it is possible to effectively inhibit leakage of the drug solution M even in a case in which the cap 14 slightly has moved in the distal direction from the state in which the cap 14 is in contact with the distal end surface 20b of the nozzle portion 20 and where the proximal end surface 43 of the base portion 42 of the inner cap 34 is slightly apart from the distal end surface 20b of the nozzle portion 20. That is, even in a case in which the proximal end surface 43 of the base portion 42 of the inner cap 34 is slightly apart from the distal end surface 20b of the nozzle portion 20 as illustrated in FIG. 4, the cylindrical wall 44 of the inner cap 34 formed of an elastic material is compressed between the outer peripheral surface 20a of the nozzle portion 20 and the inner peripheral surface 37 of the outer cap 36. This configuration allows contact between the outer peripheral surface 20a of the nozzle portion 20 and the inner peripheral surface 45 of the cylindrical wall 44, forming a liquid tight seal at a contact portion. This inhibits leakage of the drug solution M in the barrel body 12 to the outside of the cap 14.

In the present embodiment, because the axial length L of the compressed portion 52 is 0.5 mm or more, it is possible to appropriately increase the length of the liquid tight seal formed by the contact between the cylindrical wall 44 and the nozzle portion 20. This configuration makes it possible to suitably inhibit the leakage of the drug solution M to the outside of the cap 14. Furthermore, for it is possible to reliably inhibit liquid leakage in a pre-filled syringe 10 determined to be a non-defective product in a case in which a loosening length threshold for determining acceptance in the cap mounting inspection is 0.5 mm.

In the present embodiment, the compressed portion 52 includes the enlarged diameter portion 54 protruding outward in the radial direction more than the other portion of the cylindrical wall 44, making it easier to increase the contact area between the cylindrical wall 44 and the nozzle portion 20 (liquid tight seal area). In addition, the inner peripheral surface 45 of the cylindrical wall 44 has a shape substantially corresponding to the outer peripheral surface 20a of the nozzle portion 20. With this configuration, the axial length of the contact portion between the cylindrical wall 44 and the nozzle portion 20 is longer than the axial length of the enlarged diameter portion 54, making it further easier to increase the contact area between the cylindrical wall 44 and the nozzle portion 20 (liquid tight seal area). The shape substantially corresponding to the outer peripheral surface 20a of the nozzle portion 20 represents a shape that allows most of the inner peripheral surface 45 of the cylindrical wall 44 to be in contact with the outer peripheral surface 20a of the nozzle portion 20.

In the present embodiment, the axial length L of the compressed portion 52 is shorter than the axial length of the cylindrical wall 44, making it possible to effectively deter an increase in the opening torque of the cap 14 due to the presence of the compressed portion 52.

In the present embodiment, the compressed portion 52 is provided at the distal end portion of the cylindrical wall 44, leading to the formation of a liquid tight seal at the distal end portion of the outer peripheral surface 20a of the nozzle portion 20. This makes is possible to further effectively inhibit the liquid leakage to the outside of the cap 14.

With the compressibility of the compressed portion 52 at 5% to 50% in the present embodiment, it is possible to effectively deter the cap opening torque of the cap 14 from becoming excessively large while maintaining satisfactory pressure resistance performance.

Certain embodiments described herein are particularly useful in that liquid leakage can be effectively inhibited even when the diameter of the distal end opening 21 of the nozzle portion 20 is as relatively large as 1.5 mm or more. That is, with relatively large diameter of the distal end opening 21 of the nozzle portion 20, a large pressure is applied to the inner cap 34 even in a state in which the cap 14 is tightly closed (state in which the inner cap 34 and the distal end surface 20b of the nozzle portion 20 are in contact with each other). Therefore, when the diameter of a distal end opening of a nozzle portion is relatively large (for example, when the diameter is 1.5 mm or more) with a conventional cap without the compressed portion 52, the liquid leakage is likely to occur. In contrast, in according with certain embodiments described herein, liquid leakage can be effectively inhibited by the presence of the compressed portion 52 even when the diameter of the distal end opening 21 of the nozzle portion 20 is as relatively large as 1.5 mm or more.

While the above embodiment is an example in which the enlarged diameter portion 54 is provided on the outer peripheral surface of the cylindrical wall 44, or the reduced diameter portion is provided on the inner peripheral surface of the cylindrical wall 44, whereby the compressed portion 52 compressed in the radial direction is formed between the outer peripheral surface 20a of the nozzle portion 20 and the inner peripheral surface 37 of the outer cap 36. Alternatively, as illustrated in FIG. 6, the compressed portion 52a may be formed by pressing the cylindrical wall 44 by an annular protrusion 60 provided on the inner peripheral surface 37 of the outer cap 36.

Figure 6:
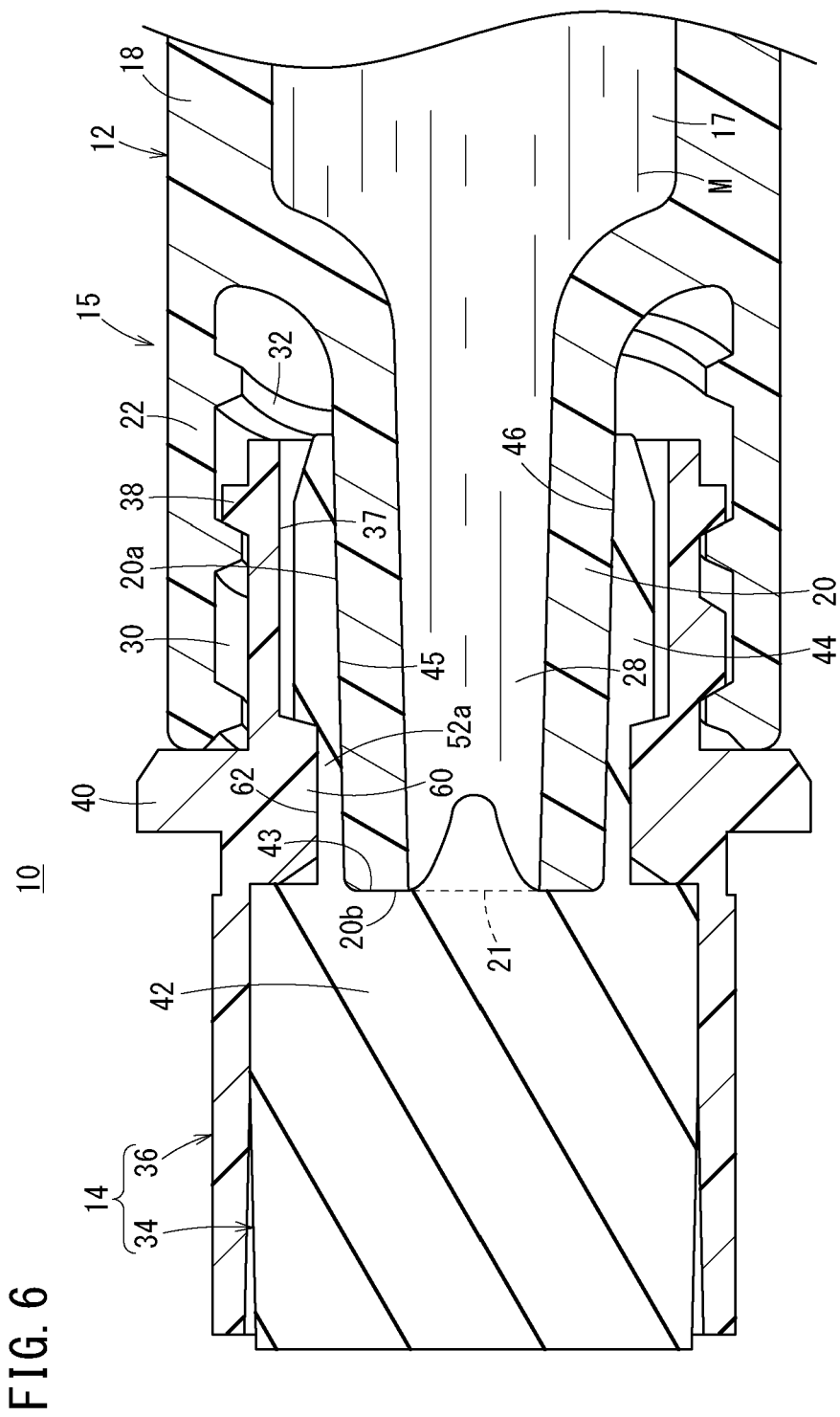
FIG. 6 is a cross sectional view of a distal end portion of a pre-filled syringe according to a modification.

Specifically, in FIG. 6, the inner peripheral surface 37 of the outer cap 36 includes the annular protrusion 60 that protrudes inward in the radial direction and presses the cylindrical wall 44. The annular protrusion 60 presses the distal end portion of the cylindrical wall 44 inward in the radial direction. The compressed portion 52a is a portion of the cylindrical wall 44, sandwiched in a compressed state between the inner peripheral surface of the annular protrusion 60 and the outer peripheral surface 20a of the nozzle portion 20.

In a state illustrated in FIG. 6 (state in which the proximal end surface 43 of the base portion 42 is in contact with the distal end surface 20b of the nozzle portion 20) and a state in which the base portion 42 is apart from the distal end surface 20b of the nozzle portion 20 by a predetermined distance (state similar to FIG. 4), the inner peripheral surface of the compressed portion 52a is in contact over a full circumference with the outer peripheral surface 20a of the nozzle portion 20, and a liquid tight seal is formed at this contact portion. This inhibits leakage of the drug solution M to the outside of the cap 14 even in a case in which the cap 14 slightly moves in the distal direction from the state of FIG. 6 and where the proximal end surface 43 of the base portion 42 is apart from the distal end surface 20b of the nozzle portion 20. Therefore, even with the configuration illustrated in FIG. 6, similar operational effects as the configuration illustrated in FIG. 3 can be obtained.

The outer peripheral portion of the inner cap 34 illustrated in FIG. 6 includes an annular groove 62 recessed inward in the radial direction, and the annular protrusion 60 is engaged with the annular groove 62. This configuration inhibits a relative movement in the axial direction between the inner cap 34 and the outer cap 36. In this manner, the annular protrusion 60 also serves as a means for inhibiting axial relative movement of the inner cap 34 and the outer cap 36, and a means for pressing the cylindrical wall 44 inward in the radial direction.

Second Embodiment

Figure 7:
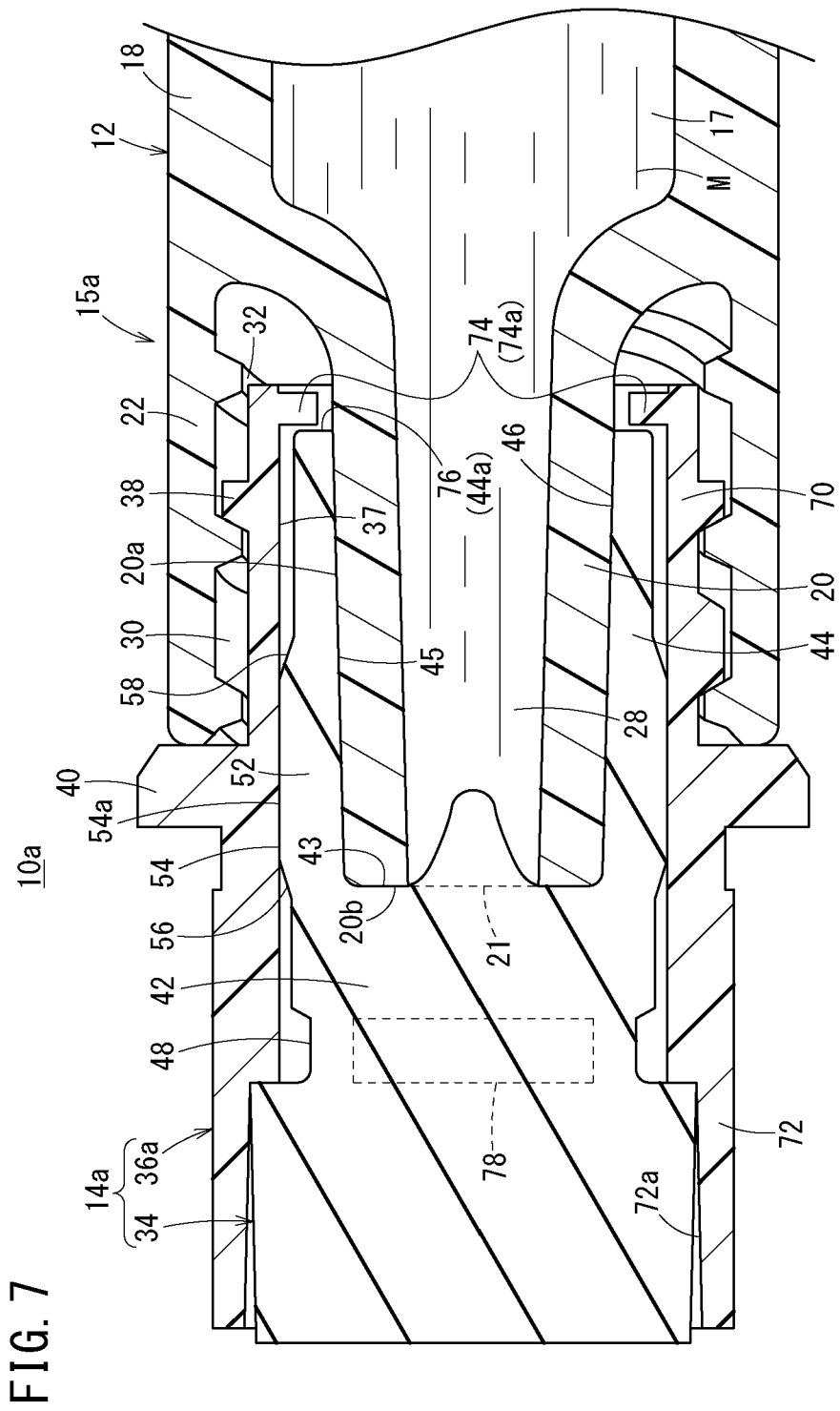
FIG. 7 is a cross sectional view of a distal end portion of a pre-filled syringe according to a second embodiment.

A cap 14a of a pre-filled syringe 10a according to a second embodiment illustrated in FIG. 7 includes: the inner cap 34 (same as the inner cap 34 illustrated in FIG. 2 or the like) for sealing the distal end opening 21; and a hollow cylindrical outer cap 36a for supporting the inner cap 34. The barrel body 12 and the cap 14a constitute a syringe barrel 15a.

The outer cap 36a includes: a proximal end cylindrical portion 70 covering the cylindrical wall 44; and a distal end cylindrical portion 72 provided on a distal side of the proximal end cylindrical portion 70 and covering the base portion 42 of the inner cap 34. The proximal end cylindrical portion 70 includes an engaging portion 74 engageable with the cylindrical wall 44 and provided on an inner peripheral surface 70a of the proximal end cylindrical portion 70. In the mounted state in which the cap 14a is mounted to the nozzle portion 20, the cylindrical wall 44 of the inner cap 34 and the proximal end cylindrical portion 70 of the outer cap 36a are inserted into the annular groove 48, and the inner peripheral surface of the cylindrical wall 44 is in contact with the outer peripheral surface 20a of the nozzle portion 20. In an unopened state of the cap 14a, the engaging portion 74 may be or need not be in contact with the cylindrical wall 44.

The engaging portion 74 is an engaging protrusion 74a protruding inward in the radial direction from the inner peripheral surface 70a of the proximal end cylindrical portion 70 of the outer cap 36a. The engaging protrusions 74a extend in the circumferential direction and is provided in plurality at intervals in the circumferential direction. In the second embodiment, two engaging protrusions 74a are provided at positions facing each other on the inner peripheral surface 70a of the proximal end cylindrical portion 70. The cylindrical wall 44 includes an engaged portion 76 engageable with the engaging protrusion 74a. The engaged portion 76 is a proximal end surface 44a of the cylindrical wall 44.

Figure 8:
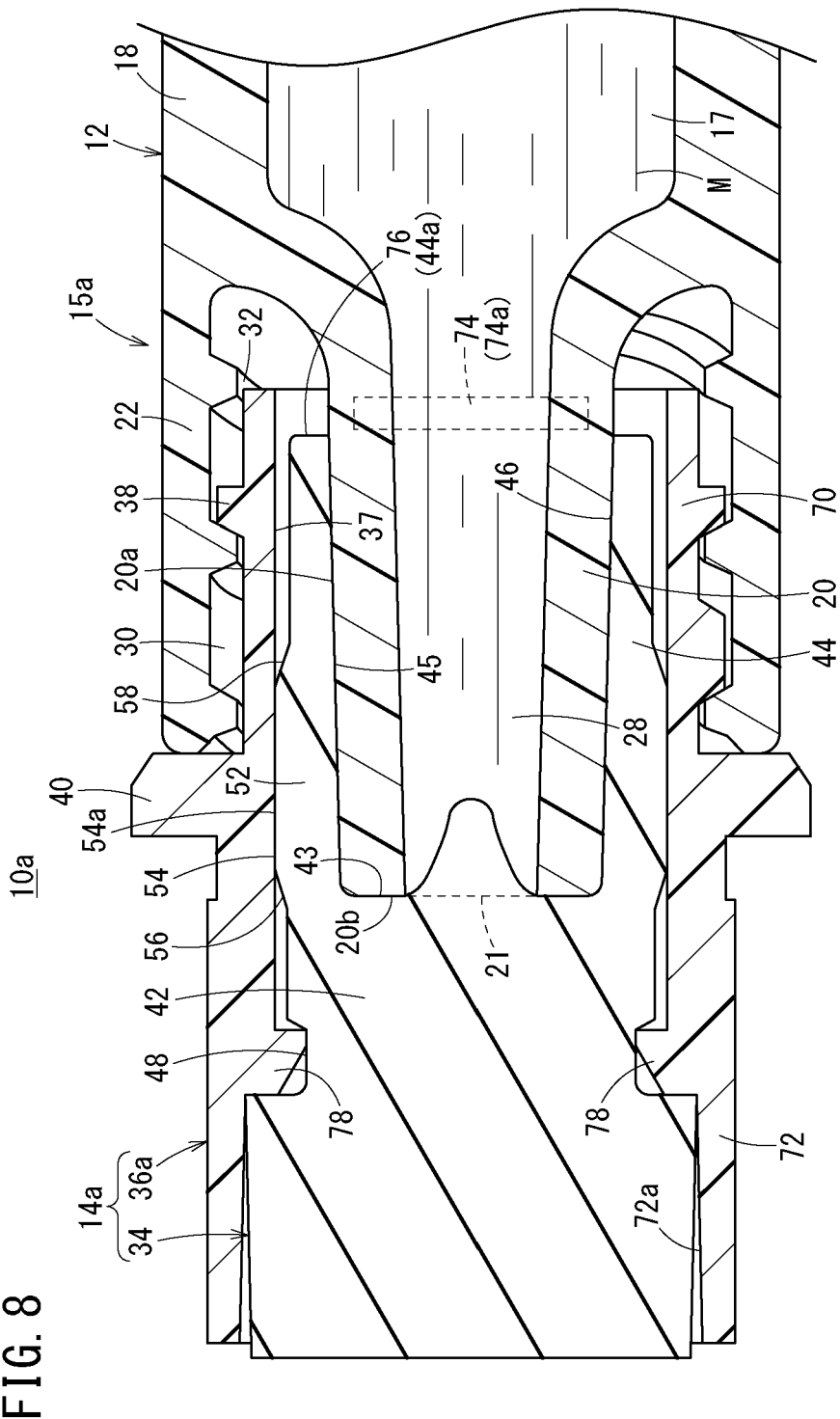
FIG. 8 is a cross sectional view of the distal end portion of the pre-filled syringe according to the second embodiment, taken at an angle different from that in FIG. 7.

As illustrated in FIG. 8, that is, in a cross section 90° axially shifted from the pre-filled syringe 10a illustrated in FIG. 7, the inner peripheral surface 72a of the distal end cylindrical portion 72 of the outer cap 36a includes two arcuate protrusions 78 protruding from the inner peripheral surface 72a inward in the radial direction and engaging with the annular groove 48 of the inner cap 34 at intervals in the circumferential direction. The arcuate protrusion 78 is a protrusion extending in an arc shape in the circumferential direction and provided in place of the above-described annular protrusion 50 (FIG. 3). The two engaging protrusions 74a and the two arcuate protrusions 78 are disposed 90° shifted with each other in the circumferential direction so as not to form an undercut at the time of injection molding.

In the above-described pre-filled syringe 10 (FIG. 3), there is a case in which the degree of contact between the outer peripheral surface 20a of the nozzle portion 20 and the inner peripheral surface of the inner cap 34 might become too high, leading to an occurrence of a pseudo fixed (adhered) state between the inner peripheral surface 20a of the nozzle portion 20 and the inner peripheral surface of the inner cap 34. Pseudo fixation (adhesion) is a state in which two members adhere to each other and a predetermined level of force or more is required to release the adhesion. In this case, in removing the cap 14a in the mounted state from the barrel body 12, the cylindrical wall 44 of the inner cap 34 expands and causes the cap 14a to be removed after full expansion of the cylindrical wall 44, leading to spouting out of the drug solution M from the inside of the barrel body 12. Spouting out of the drug solution M might decrease the liquid amount and cause the drug solution M to be attached to the surroundings.

In contrast, according to the pre-filled syringe 10a, when the cap 14a in the mounted state is removed from the barrel body 12, the engagement between the engaging portion 74 and the cylindrical wall 44 allows the moving force of the outer cap 36a in moving toward the lock adapter 22 to be transmitted directly to the cylindrical wall 44. That is, when the cylindrical wall 44 expands at the time of opening the cap 14a to move with the outer cap 36a alone, the engaging protrusion 74a of the outer cap 36a is caught on the inner cap 34.

According to this configuration, it is possible to move the inner cap 34 together with the movement of the outer cap 36a at removal of the cap 14a from the barrel body 12 even when the inner peripheral surface of the cylindrical wall 44 of the inner cap 34 is pseudo fixed (adhered) to the outer peripheral surface 20a of the nozzle portion 20, making it possible to inhibit (or prevent) expansion of the cylindrical wall 44. This makes is possible to inhibit the drug solution M from spouting out at the time of opening the cap 14a.

Particularly, in the pre-filled syringe 10a, the engaging portion 74 is the engaging protrusion 74a protruding inward in the radial direction from the inner peripheral surface 70a of the proximal end cylindrical portion 70 of the outer cap 36a, and the cylindrical wall 44 includes the engaged portion 76 to be engaged with the engaging protrusion 74a. At removal of the cap 14a in the mounted state from the barrel body 12, engagement of the engaging protrusion 74a with the engaged portion 76 from the proximal side allows the moving force to be transmitted directly to the cylindrical wall 44. This configuration enables acquisition of a further satisfactory engaging force, making it possible to further reliably move the inner cap 34 together with the movement of the outer cap 36a when the cap 14a is removed from the barrel body 12.

In the pre-filled syringe 10a, the engaged portion 76 is the proximal end surface 44a of the cylindrical wall 44. With this configuration, the proximal end surface 44a of the cylindrical wall 44 is pressed in the distal direction by the engaging portion 74 when the cap 14a is removed from the barrel body 12, making it possible to move the entire cylindrical wall 44 integrally with the outer cap 36a. In addition, the proximal end surface 44a of the cylindrical wall 44 can be utilized as it is as the engaged portion 76, making it possible to avoid complication of the structure of the cylindrical wall 44 due to the presence of the engaged portion 76.

The barrel body 12 is formed of a cyclic olefin polymer or a cyclic olefin copolymer. With the barrel body 12 formed of a cyclic olefin polymer or a cyclic olefin copolymer, the inner cap 34 is likely to be pseudo fixed to the nozzle portion 20. Accordingly, in this aspect, it is possible to deter expansion of the cylindrical wall 44 at the time of opening the cap 14a is particularly useful. With the inner cap 34 formed from butyl rubber, the inner cap 34 is further likely to be pseudo fixed to the nozzle portion 20, making the present embodiment further useful.

Sterilization treatment (for example, high pressure steam sterilization), in which the syringe barrel is heated, 15a has been applied on the syringe barrel 15a in the mounted state. With application of sterilization treatment involving heating, the inner cap 34 is further likely to be pseudo fixed to the nozzle portion 20. Accordingly, in this aspect, it is possible to deter expansion of the cylindrical wall 44 at the time of opening the cap 14a is particularly useful.

Third Embodiment

Figure 9:
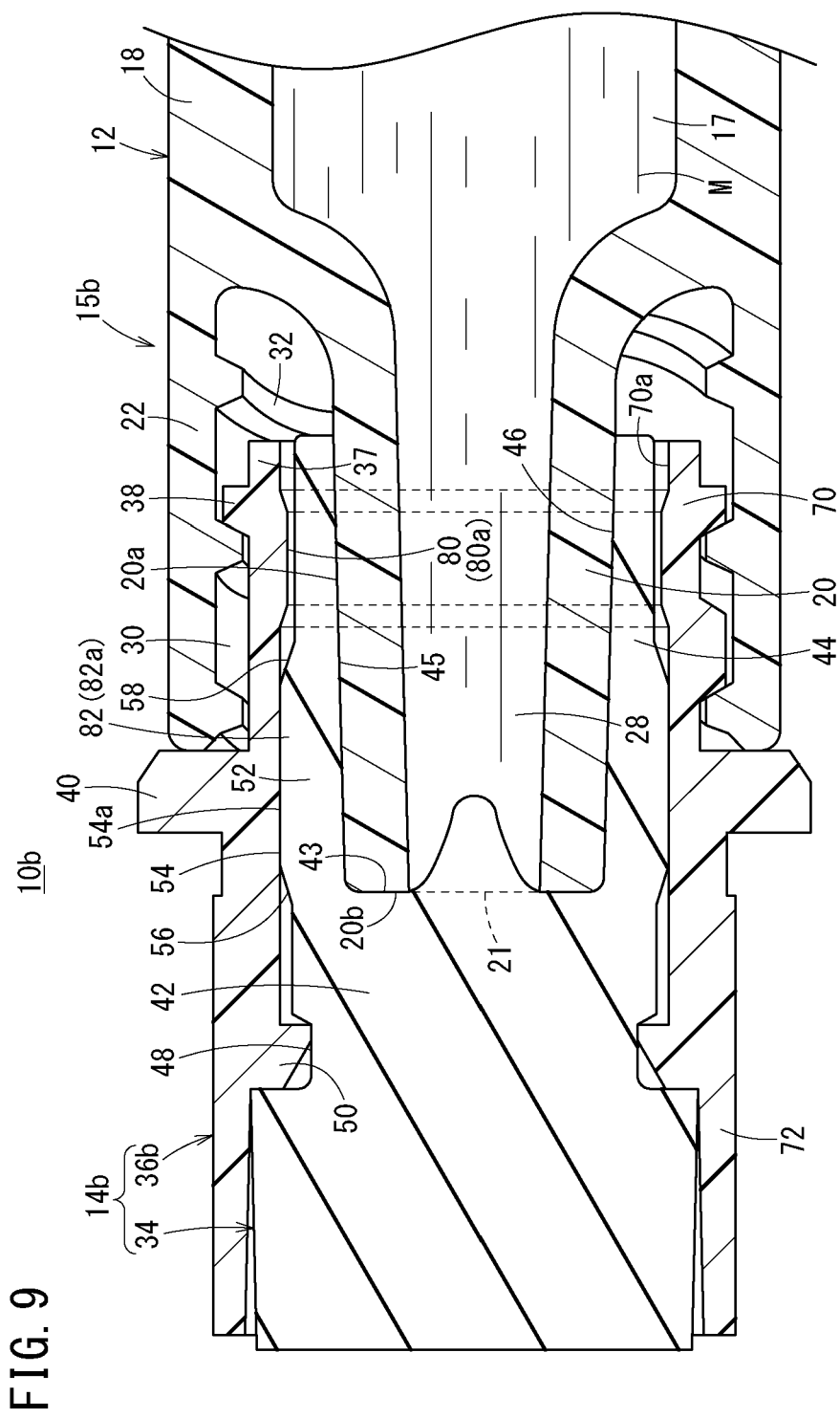
FIG. 9 is a cross sectional view of a distal end portion of a pre-filled syringe according to a third embodiment.

A cap 14b of a pre-filled syringe 10b according to a third embodiment illustrated in FIG. 9 includes: the inner cap 34 (same as the inner cap 34 illustrated in FIG. 2 or the like) for sealing the distal end opening 21; and a hollow cylindrical outer cap 36b for supporting the inner cap 34. The barrel body 12 and the cap 14b constitute a syringe barrel 15b.

The proximal end cylindrical portion 70 of the outer cap 36b includes an engaging portion 80 engageable with the cylindrical wall 44 and provided on the inner peripheral surface 70a of the proximal end cylindrical portion 70. The engaging portion 80 is an engaging protrusion 80a protruding inward in the radial direction from the inner peripheral surface 70a of the proximal end cylindrical portion 70 of the outer cap 36a. The engaging protrusion 80a is an annular protrusion extending over the entire circumference in the circumferential direction.

The cylindrical wall 44 includes an engaged portion 82 engageable with the engaging protrusion 80a. The engaged portion 82 is an engaged protrusion 82a protruding outward in the radial direction from the outer peripheral surface of the cylindrical wall 44 and is provided on a distal side of the engaging protrusion 74a. In FIG. 9, the enlarged diameter portion 54 constitutes the engaged protrusion 82a. Note that the engaged protrusion 82a may be provided on more proximal side than the enlarged diameter portion 54, separately from the enlarged diameter portion 54. When the engaged protrusion 82a is provided separately from the enlarged diameter portion 54, the engaging portion 80

(engaging protrusion 80a) is provided on a proximal side of the position illustrated in FIG. 9.

According to the pre-filled syringe 10b, when the cap 14b in the mounted state is removed from the barrel body 12, engagement between the engaging protrusion 80a and the engaged protrusion 82a allows the moving force of the outer cap 36b in moving toward the lock adapter 22 to be transmitted directly to the cylindrical wall 44. That is, when the cylindrical wall 44 expands at the time of opening the cap 14b to move with the outer cap 36b alone, the engaging protrusion 80a of the outer cap 36b is caught on the engaged protrusion 82a of the inner cap 34 (cylindrical wall 44). This can minimize the expansion of the cylindrical wall 44, making it possible to inhibit the drug solution M from spouting out at the time of opening the cap 14b.

Fourth Embodiment

Figure 10:
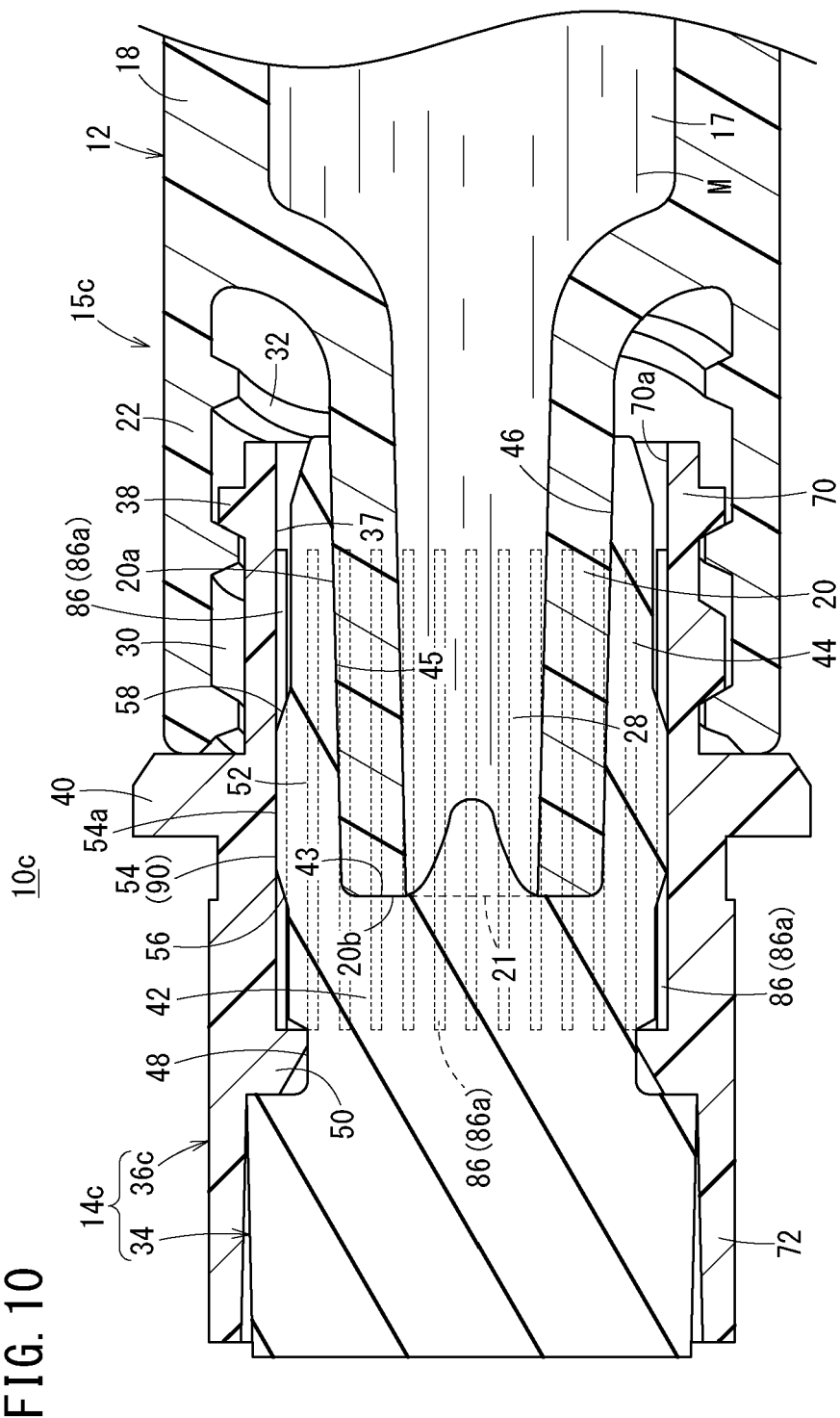
FIG. 10 is a cross sectional view of a distal end portion of a pre-filled syringe according to a fourth embodiment.

A cap 14c of a pre-filled syringe 10c according to a fourth embodiment illustrated in FIG. 10 includes: the inner cap 34 (same as the inner cap 34 illustrated in FIG. 2 or the like) for sealing the distal end opening 21; and a hollow cylindrical outer cap 36c for supporting the inner cap 34. The barrel body 12 and the cap 14c constitute a syringe barrel 15c.

Figure 11:
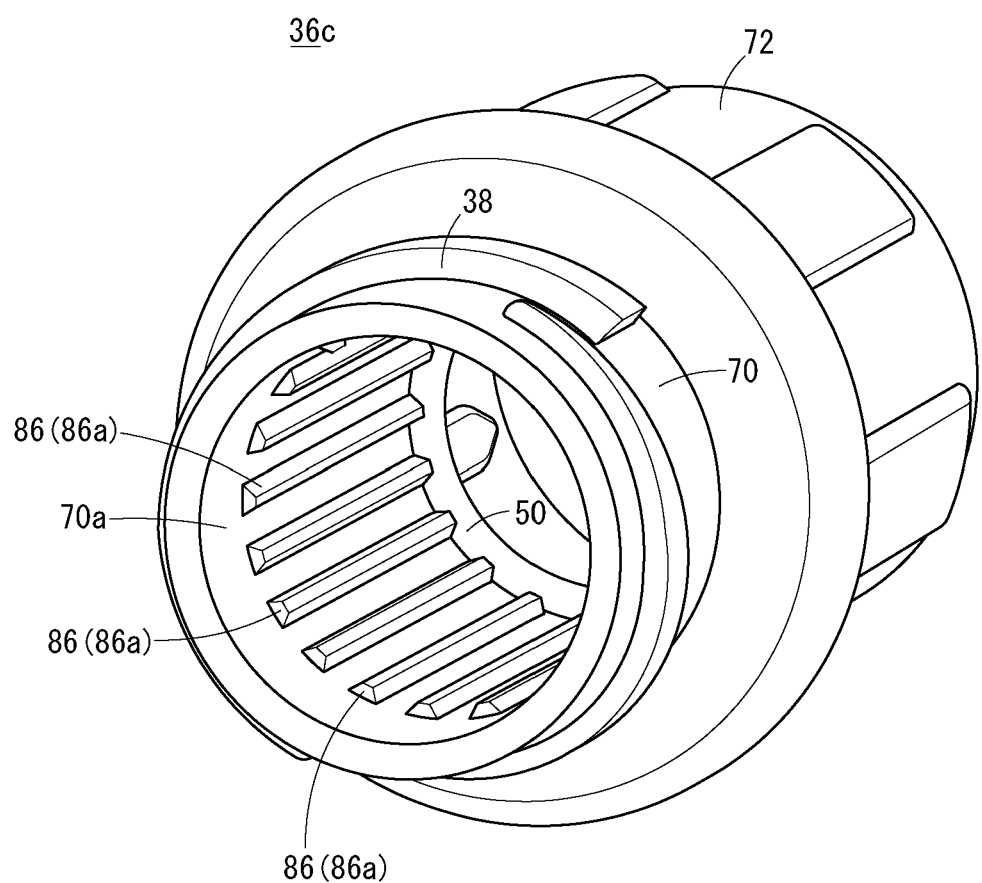
FIG. 11 is a perspective view of an outer cap of the pre-filled syringe illustrated in FIG. 10.

The proximal end cylindrical portion 70 of the outer cap 36c includes an engaging portion 86 engageable with the cylindrical wall 44 and provided on the inner peripheral surface 70a of the proximal end cylindrical portion 70. The engaging portion 86 is a plurality of engaging ribs 86a extending along the axis of the proximal end cylindrical portion 70. As illustrated in FIG. 11, the plurality of engaging ribs 86a is arranged at intervals in the circumferential direction.

In FIG. 10, the cylindrical wall 44 includes an engaged portion 90 engaged with the plurality of engaging ribs 86a, on the outer peripheral surface of the cylindrical wall 44. The plurality of engaging ribs 86a bites into the engaged portion 90. In FIG. 10, the enlarged diameter portion 54 constitutes the engaged portion 90. Note that the engaged portion 90 may be provided on more proximal side than the enlarged diameter portion 54, separately from the enlarged diameter portion 54. An engaged rib meshed with the engaged rib 86a may be provided on the outer peripheral surface of the cylindrical wall 44. In this case, the engaged rib extends along the axis of the cylindrical wall 44 and is provided in plurality at intervals in the circumferential direction.

According to the pre-filled syringe 10c, when the outer cap 36c is rotated with respect to the lock adapter 22 to remove the cap 14c in the mounted state from the barrel body 12, engagement of the plurality of engaging ribs 86a with the engaged portion 90 (outer peripheral surface of the cylindrical wall 44) allows the moving force of the outer cap 36c in rotationally moving with respect to the lock adapter 22 to be transmitted directly to the cylindrical wall 44. This rotates the cylindrical wall 44 of the inner cap 34 simultaneously with the outer cap 36c when the cap 14c is removed from the barrel body 12. Accordingly, moving the cylindrical wall 44 along with the movement of the outer cap 36c makes it possible to inhibit expansion of the cylindrical wall 44. This makes is possible to inhibit the drug solution M from spouting out at the time of opening the cap 14c.

The present invention is not limited to the above-described embodiment, and various modifications are possible without departing from the scope and spirit of the present invention.

Unlike the above-described embodiment, in a pre-filled syringe (syringe barrel) according to a reference example, there is no need to allow the cylindrical wall 44 to be sandwiched, in the compressed state, between the outer peripheral surface 20a of the nozzle portion 20 and the inner peripheral surface of the outer cap in the state in which the base portion 42 is in contact with the distal end surface 20b of the nozzle portion 20 and the state in which the base portion 42 is in a state of being apart from the distal end surface 20b of the nozzle portion 20 by a predetermined distance (that is, the compressed portion 52 may be omitted). Even in this case, it is still possible to inhibit the drug solution M from spouting out at the time of opening the plug in a case in which there is provided the above configuration (FIG. 7 to FIG. 10) in which engagement between the engaging portion and the cylindrical wall 44 allows the moving force of the outer cap in moving toward the lock adapter 22 to be transmitted directly to the cylindrical wall 44 when the cap in the mounted state is removed from the barrel body 12.

What is claimed is:
1. A syringe barrel comprising:
a barrel body comprising a nozzle portion at a distal end thereof; and
a cap removably mounted to the nozzle portion and configured to seal a distal end opening of the nozzle portion,
wherein the cap comprises:
an inner cap formed of an elastic material and configured to come in liquid tight contact with the nozzle portion in a mounted state in which the cap is mounted to the nozzle portion, and
a cylindrical outer cap formed of a material having a higher hardness than the inner cap and fixed around the inner cap;
wherein the inner cap comprises:
a base portion, and
a cylindrical wall extending from the base portion in a proximal direction and surrounding the nozzle portion; and
wherein, in a state in which the base portion is in contact with a distal end surface of the nozzle portion and in a state in which the base portion is apart from the distal end surface of the nozzle portion by a predetermined distance, a distal end portion of the cylindrical wall extends circumferentially around a distal end of the nozzle portion and comprises a compressed portion that is compressed between (i) an outer peripheral surface of the distal end of the nozzle portion and (ii) an inner peripheral surface of the outer cap, such that the cylindrical wall is in liquid tight contact over a full circumference with the outer peripheral surface of the distal end of the nozzle portion, wherein the compressed portion is in direct contact with both (i) the outer peripheral surface of the distal end of the nozzle portion and (ii) the inner peripheral surface of the outer cap;
wherein an axial length of the compressed portion is shorter than an axial length of the cylindrical wall; and
wherein the axial length of the compressed portion is 0.5 mm or more.

2. The syringe barrel according to claim 1,
wherein the compressed portion comprises an enlarged diameter portion protruding outward in a radial direction more than a portion of the cylindrical wall other than the compressed portion.

3. The syringe barrel according to claim 2,
wherein an inner peripheral surface of the cylindrical wall has a shape substantially corresponding to the outer peripheral surface of the nozzle portion.

4. The syringe barrel according to claim 1,
wherein a compressibility of the compressed portion, is in a range of 5% to 50%.

5. The syringe barrel according to claim 1,
wherein a diameter of the distal end opening of the nozzle portion is 1.5 mm or more.

6. The syringe barrel according to claim 1,
wherein the barrel body comprises:
  a lock adapter disposed on an outer side of the nozzle portion, and
  an annular recess disposed between the nozzle portion and the lock adapter and recessed in the proximal direction;
wherein the outer cap comprises a proximal end cylindrical portion covering the cylindrical wall;
wherein the proximal end cylindrical portion of the outer cap comprises an engaging portion on an inner peripheral surface of the proximal end cylindrical portion, the engaging portion being configured to engage with the cylindrical wall;
wherein, in the mounted state, the cylindrical wall of the inner cap and the proximal end cylindrical portion of the outer cap are inserted into the annular recess, and an inner peripheral surface of the cylindrical wall is in contact with the outer peripheral surface of the nozzle portion; and
wherein, when the cap in the mounted state is removed from the barrel body, engagement between the engaging portion and the cylindrical wall allows a moving force of the outer cap, in moving with respect to the lock adapter, to be transmitted directly to the cylindrical wall.

7. The syringe barrel according to claim 6,
wherein the engaging portion comprises an engaging protrusion that protrudes inward in a radial direction from the inner peripheral surface of the proximal end cylindrical portion of the outer cap;
wherein the cylindrical wall comprises an engaged portion that is configured to engage with the engaging protrusion; and
wherein, when the cap in the mounted state is removed from the barrel body, engagement of the engaging protrusion with the engaged portion allows the moving force to be transmitted directly to the cylindrical wall.

8. The syringe barrel according to claim 7,
wherein the engaged portion is a proximal end surface of the cylindrical wall.

9. The syringe barrel according to claim 7,
wherein the engaged portion is an engaged protrusion that protrudes outward in the radial direction from an outer peripheral surface of the cylindrical wall.

10. The syringe barrel according to claim 6,
wherein the lock adapter comprises a female screw portion at an inner peripheral surface of the lock adapter;
wherein the outer cap comprises a male screw portion that is disposed on an outer peripheral surface of the proximal end cylindrical portion, the male screw portion being configured to be screwed together with the female screw portion in the mounted state;
wherein the engaging portion comprises a plurality of engaging ribs extending along an axis of the proximal end cylindrical portion;
wherein the cylindrical wall comprises an engaged portion that is disposed on an outer peripheral surface of the cylindrical wall, the engaged portion being configured to be engaged with the plurality of engaging ribs; and
wherein, when the outer cap is rotated with respect to the lock adapter to remove the cap in the mounted state from the barrel body, engagement between the plurality of engaging ribs and the engaged portion allows the moving force of the outer cap, in rotationally moving with respect to the lock adapter, to be transmitted directly to the cylindrical wall.

11. The syringe barrel according to claim 6,
wherein the barrel body is formed of one of a cyclic olefin polymer and a cyclic olefin copolymer.

12. The syringe barrel according to claim 11,
wherein the inner cap is formed of butyl rubber.

13. The syringe barrel according to claim 6,
wherein sterilization treatment, in which the syringe barrel is heated, has been applied on the syringe barrel in the mounted state.

14. A pre-filled syringe comprising:
the syringe barrel according to claim 1;
a gasket slidably inserted in the barrel body;
a plunger coupled to or couplable to the gasket; and
a drug solution filled in a liquid chamber formed by the barrel body and the gasket.

15. A method for manufacturing the syringe barrel according to claim 1, the method comprising:
  an assembling step of mounting the cap to the barrel body to assemble a barrel assembly;
  a photographing step of photographing a reference portion of the barrel body and a reference portion of the cap as one image using a camera; and
  a determination step of determining that the barrel assembly is non-defective if a distance between the reference portion of the barrel body and the reference portion of the cap is a predetermined value or less in the image photographed by the camera,
wherein the axial length of the compressed portion is the predetermined value or more.

* * * * *